United States Patent
Leigh et al.

(10) Patent No.: US 8,565,899 B1
(45) Date of Patent: Oct. 22, 2013

(54) IMPLANTABLE PROSTHESIS CONFIGURATION TO CONTROL HEAT DISSIPATION FROM PROSTHESIS COMPONENTS

(75) Inventors: Charles Roger Aaron Leigh, Sydney (AU); Scott Henshaw, Sydney (AU)

(73) Assignee: Cochlear Limited (AU)

( * ) Notice: Subject to any disclaimer, the term of this patent is extended or adjusted under 35 U.S.C. 154(b) by 0 days.

(21) Appl. No.: 13/449,426

(22) Filed: Apr. 18, 2012

(51) Int. Cl.
*A61N 1/00* (2006.01)

(52) U.S. Cl.
USPC .......................................... 607/137

(58) Field of Classification Search
USPC .................... 607/137, 55, 116, 121
See application file for complete search history.

(56) References Cited

U.S. PATENT DOCUMENTS

| | | | |
|---|---|---|---|
| 4,149,542 A * | 4/1979 | Thoren | 607/121 |
| 4,352,360 A * | 10/1982 | King | 607/121 |
| 7,363,090 B2 | 4/2008 | Halperin | |
| 7,974,700 B1 * | 7/2011 | Gibson | 607/55 |
| 8,000,801 B2 | 8/2011 | Stevenson | |
| 8,364,281 B2 * | 1/2013 | Duncan et al. | 607/116 |
| 2010/0160997 A1 | 6/2010 | Johnson | |

* cited by examiner

*Primary Examiner* — Robert N Wieland
(74) *Attorney, Agent, or Firm* — McDonnell Boehnen Hulbert & Berghoff LLP

(57) ABSTRACT

Disclosed herein are medical prostheses including a cochlear implant that includes circuitry enclosed within a housing and at least one electrode lead extending from the housing. The electrode lead comprises a conducting pathway and an electrode terminal at one end of the electrode lead. The conducting pathway connects the circuitry with the electrode terminal, and insulation (or an insulating sleeve) encloses at least a portion of the conducting pathway. In some embodiments, the electrode terminal has a lower thermal conductivity relative to the implant housing. In further embodiments, the insulation has thermal conductivity and thermal conduction properties that cause at least some thermal energy in the conducting pathway to flow into the insulation rather than to the electrode terminal. In still further embodiments, at least one of the electrode terminal or the electrode lead includes at least one thermal mass enhancing structure.

18 Claims, 3 Drawing Sheets

IMPLANTABLE PROSTHESIS CONFIGURATION TO CONTROL HEAT DISSIPATION FROM PROSTHESIS COMPONENTS

BACKGROUND

Various types of hearing prostheses provide persons with different types of hearing loss with the ability to perceive sound. Hearing loss may be conductive, sensorineural, or some combination of both conductive and sensorineural hearing loss. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing aids. An acoustic hearing aid typically includes a small microphone to detect sound, an amplifier to amplify certain portions of the detected sound, and a small speaker to transmit the amplified sounds into the person's ear. Vibration-based hearing aids typically include a small microphone to detect sound, and a vibration mechanism to apply vibrations corresponding to the detected sound to a person's bone, thereby causing vibrations in the person's inner ear, thus bypassing the person's auditory canal and middle ear. Vibration-based hearing aids include bone conduction auditory prostheses, direct acoustic stimulation devices, or other vibration-based devices. A bone conduction auditory prosthesis typically utilizes a surgically-implanted mechanism to transmit sound via direct vibrations of the skull. Similarly, a direct acoustic stimulation device typically utilizes a surgically-implanted mechanism to transmit sound via vibrations corresponding to sound waves to generate fluid motion in a person's inner ear. Other non-surgical vibration-based hearing aids use similar vibration mechanisms to transmit sound via direct vibration of teeth or other cranial or facial bones.

Persons with certain forms of sensorineural hearing loss may benefit from cochlear implants and/or auditory brainstem implants. For example, cochlear implants provide a person having sensorineural hearing loss with the ability to perceive sound by stimulating the person's auditory nerve via an electrode array implanted in the person's cochlea. In traditional cochlear implant systems, an external component of the cochlear implant detects sound waves, which are converted into a series of electrical stimulation signals delivered to the implant recipient's cochlea via the electrode array. Electrically stimulating auditory nerves in a cochlea with a cochlear implant enables persons with sensorineural hearing loss to perceive sound.

A traditional cochlear implant system includes an external speech processor unit worn on the body of a prosthesis recipient and a stimulator unit implanted in the mastoid bone of the recipient. In this traditional configuration, the external speech processor unit detects external sound and converts the detected sound into a coded signal through a suitable speech processing strategy. The coded signal is sent to the implanted stimulator unit via a transcutaneous link. The stimulator unit (i) processes the coded signal, (ii) generates a series of stimulation signals based on the coded signal, and (iii) applies the stimulation signals to the recipient's auditory nerve via electrodes.

In another example cochlear implant, the functionality of the external speech processor unit and the implanted stimulator unit are combined into a single implantable housing to create a totally implantable cochlear implant (TICI). The TICI system can be either a monolithic system containing all the components in a single implant housing or a collection of implant housings coupled together. In operation, detected sound is processed by a speech processor in the TICI system, and stimulation signals are delivered to the recipient via the electrodes without the need for a transcutaneous transmission of signals between an external speech processor unit and an implanted stimulator unit as in the traditional cochlear implant configuration described previously.

Certain types of radio frequency (RF) signals, such as signals generated by magnetic resonance imaging (MRI) systems, present risks for recipients of implantable medical devices such as the cochlear implant devices described above. MRI is a medical imaging technique used to visualize detailed internal structures of a person's body. Because MRI provides good visual contrast between different soft tissues of the body, MRI can be especially useful in imaging the brain, muscles, and heart, for example. In operation, an MRI machine uses a powerful magnetic field to align the magnetization of particular atomic nuclei in the human body, and an RF field to systematically alter the alignment of the magnetization to cause the magnetized nuclei to produce a rotating magnetic field that is detectable by a special scanner. In some circumstances, the RF field generated by the MRI system can induce circulating currents in implant electrode leads at certain RF frequencies. In particular, the electrode leads act as antennas in the presence of the RF field generated by the MRI system. An electrode lead collects RF energy that, in typical systems, is dissipated as heat at localised areas such as the electrode tip. If the electrode tip gets too hot, the electrode tip can damage surrounding tissue and injure the implant recipient. Other types of implantable prostheses having structures or components susceptible to induced currents can pose similar dangers to prosthesis recipients.

Prior approaches for reducing localised heat dissipation to avoid injury to implant recipients have focused on reducing the circulating currents caused by RF fields by changing electrical circuit parameters of the electrode lead in response to MRI-specific frequencies. For example, electrode leads in prior systems have included resonant tank circuits configured as band-stop filters, which resonate and open circuit at a specified frequency. Other prior systems have additionally or alternatively included electromagnetic interference (EMI) filters at the electrode lead ingress and egress to the implant housing to form a low impedance at a specified frequency which in turn causes currents induced by the RF field to be shunted into the implant package.

SUMMARY

It is desired to ameliorate the problem of localized thermal energy dissipation caused by RF field-induced currents in the electrode leads.

In accordance with some of the disclosed embodiments, thermal energy (heat) is directed away from the electrode tip of an extra-cochlear electrode lead of a cochlear implant system, and toward at least one of (i) the insulating sleeve of the extra-cochlear electrode lead or (ii) the implant housing. Some embodiments include an electrode tip that has a lower thermal conductivity than the thermal conductivity of the insulating sleeve of the extra-cochlear electrode lead and/or the implant housing. Preferably, the thermal conductivity and thermal conduction properties of the insulating sleeve cause at least some thermal energy generated by RF field-induced currents to flow into the insulating sleeve rather than to the electrode tip. Still other embodiments additionally or alternatively include an electrode tip configuration that has a greater thermal mass than traditional electrode tip configurations.

Both the traditional cochlear implant configuration and the TICI configuration are typically configured to apply stimulation signals to a recipient's cochlea via an intra-cochlear lead having an array of pads or terminals, and at least one extra-cochlear lead having a platinum ball or a bullet shaped electrode at the distal end. Intra-cochlear electrodes are positioned inside the recipient's cochlea and extra-cochlear electrodes are positioned outside of the recipient's cochlea. The extra-cochlear lead is typically arranged so that the electrode tip (or terminal) is electrically coupled to stimulation circuitry within the implant housing and at least partially enclosed within insulation or insulating sleeve. The intra-cochlear lead is typically arranged so that each individual electrode pad or terminal is electrically coupled to stimulation circuitry within the implant housing via a conducting member and at least partially enclosed within insulation or an insulating sleeve. In accordance with some of the disclosed embodiments, thermal energy (heat) is directed away from the electrode pads or terminals, and toward at least one of (i) the insulation or insulating sleeve or (ii) the implant housing.

DETAILED DESCRIPTION

Figure 1A:
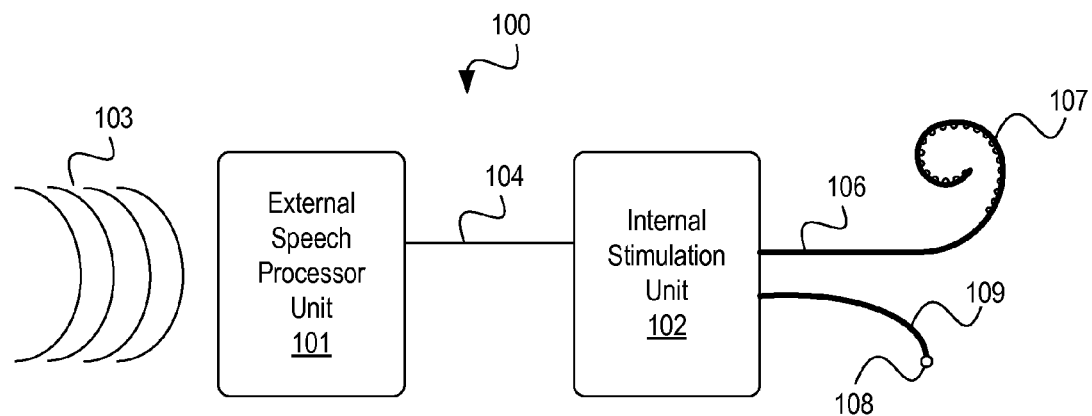
FIG. 1A shows an example of a traditional cochlear implant system according to some embodiments.

FIG. 1A shows an example of a traditional type of cochlear implant system 100 according to some embodiments. The traditional cochlear implant system 100 includes an external speech processor unit 101 and an internal stimulation unit 102 implanted in a recipient. The internal stimulation unit 102 is enclosed within a biocompatible housing (implant housing) constructed of a metal, metal alloy or ceramic material. The external speech processor unit 101 includes sound detection circuitry (not shown) configured to detect external sound 103 and sound processing circuitry (not shown) configured to convert the detected sound 103 into a coded signal according to a speech processing strategy. The external speech processor unit 101 sends the coded signal (not shown) to the internal stimulation unit 102 via a transcutaneous communications link 104. The internal stimulation unit 102 includes stimulation circuitry (not shown) configured to generate stimulation signals based on the coded signal (not shown), and apply the stimulation signals to the implant recipient's cochlea via (i) an electrode array 106 that includes a plurality of intra-cochlear electrode pads or terminals 107 configured to be positioned within the implant recipient's cochlea and (ii) one or more extra-cochlear electrodes. The intra-cochlear electrode pads or terminals 107 are typically configured to function as "active" (current source) electrodes, and the one or more extra-cochlear electrodes are typically configured to function as "reference" (current sink) electrodes.

The traditional cochlear implant system 100 shown in FIG. 1A includes an extra-cochlear electrode having an extra-cochlear electrode lead 109 terminating in an electrode tip 108 (sometimes referred to as a "ball" electrode) at the distal end of the electrode lead 109. The electrode tip 108 is configured to be positioned beneath muscle tissue near the implant recipient's cochlea.

Figure 1B:
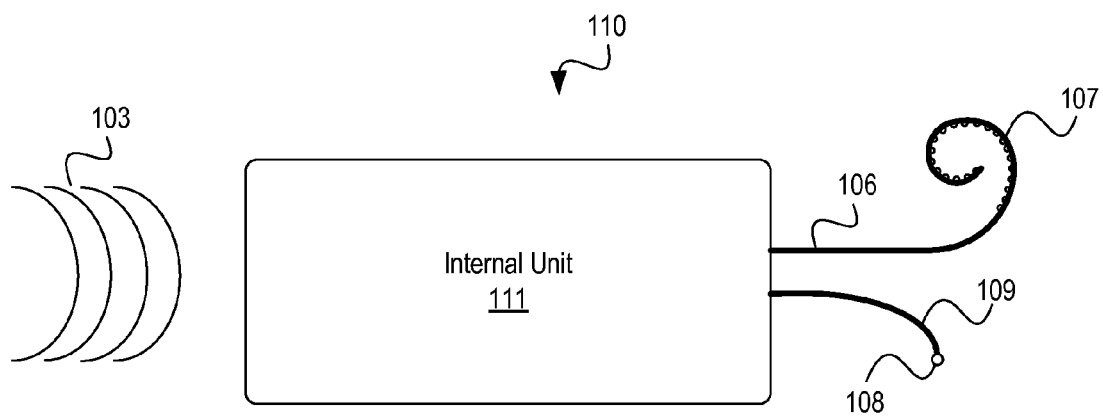
FIG. 1B shows an example of a totally implantable cochlear implant (TICI) system according to some embodiments.

FIG. 1B shows an example of a totally implantable cochlear implant (TICI) system 110 according to some embodiments. The TICI system 110 includes a fully-implantable internal unit 111 that performs the sound detection, speech processing, and stimulation functions similar to the external speech processor unit 101 and internal stimulation unit 102 of the traditional cochlear implant system 100 shown in FIG. 1A. But because the sound detection, speech processing, and stimulation functions are housed within the single internal unit 111, there is no need to transmit coded signals between external and internal units via a transcutaneous link as is the case with traditional cochlear implant embodiments. In operation, the internal unit 111 includes sound detection circuitry (not shown) configured to detect external sound 103 and sound processing circuitry (not shown) configured to convert the detected sound 103 into a coded signal according to a speech processing strategy. The internal unit 111 also includes stimulation circuitry (not shown) configured to generate stimulation signals based on the coded signal, and apply the stimulation signals to the implant recipient's cochlea via electrodes. In particular, like the traditional cochlear implant 100 of FIG. 1A, the TICI 110 of FIG. 1B is also configured to apply the stimulation signals to the implant recipient via (i) an electrode array 106 that includes a plurality of intra-cochlear electrode pads or terminals 107 configured to be positioned within the implant recipient's cochlea and (ii) one or more extra-cochlear electrodes. The TICI system 110 shown in FIG. 1B also includes an extra-cochlear electrode that is substantially similar to the extra-cochlear electrode shown and described within respect to FIG. 1A.

As with the traditional cochlear implant 100 in FIG. 1A, the intra-cochlear electrode pads or terminals 107 of the TICI 110 are typically configured to function as "active" (current source) electrodes, and the one or more extra-cochlear electrodes of the TICI 110 are typically configured to function as "reference" (current sink) electrodes.

Figure 2:
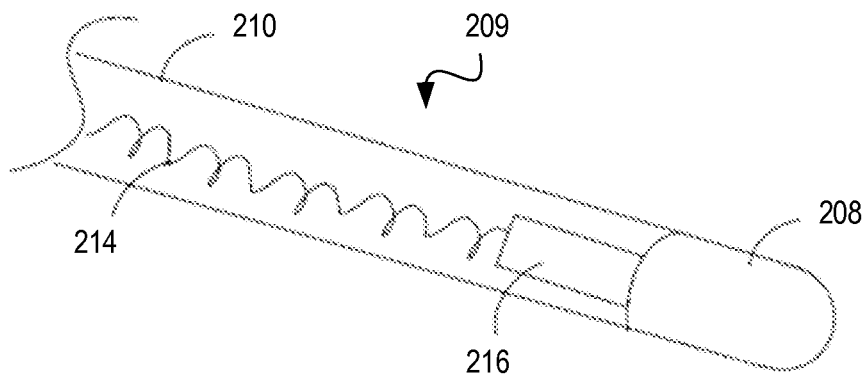
FIG. 2 shows an example of an electrode lead with an electrode tip according to some embodiments.

FIG. 2 shows an example of an extra-cochlear electrode lead 209 with an electrode tip 208 according to some embodiments. The electrode lead 209 includes a conducting pathway 214 enclosed within insulation 210, or an insulating sleeve 210. The proximal end (not shown) of the conducting pathway 214 is connected to stimulation circuitry enclosed within an implant housing. The conducting pathway 214 is an electrically conductive wire or similar structure made from a conductive material, such as platinum for example, and provides an electrically conductive path between the stimulation circuitry (in the implant housing) and the electrode tip 208. In the embodiment shown in FIG. 2, the electrode tip 208 is coupled to the conducting pathway 214 via a crimp 216. However, in other embodiments, the electrode tip 208 can be coupled to the conducting pathway 214 via other connection mechanisms such as welds, clips, or other similar connection mechanisms now known or later developed.

In some embodiments, the electrode tip 208 is a metal or metal alloy having a thermal conductivity that is lower than the thermal conductivity of the implant housing. Thermal conductivity is one measure of a material's ability to conduct heat. A material having a higher thermal conductivity will conduct heat better than a material having a lower thermal conductivity.

In one embodiment, for example, the electrode tip 208 is made at least partially from a titanium alloy (e.g., titanium grade 5, titanium grade 23, or other biocompatible titanium alloy) having a thermal conductivity of about 7.2 watts per meter kelvin (W/m·K) or less, and the implant housing is configured to have a thermal conductivity value of about 70 W/m·K. The thermal conductivity of the implant housing is based on the thermal conductivity of the combination of the materials of the stimulation circuitry enclosed within the implant housing, the materials that connect the conducting pathway 214 to the stimulation circuitry, and the material of the implant housing itself. These materials are generally referred to as housing materials. Examples of housing materials include platinum and copper, but other materials could be used as well.

In another embodiment, the electrode tip 208 is commercially-pure titanium, which has a thermal conductivity of about 16.3 W/m·K to about 21.6 W/m·K. In still another embodiment, the electrode tip 208 is steel, which has a thermal conductivity of about 16.0 W/m·K. Other combinations of materials selected for the electrode tip 208 and the housing materials are possible as well, such that the electrode tip 208 has a lower thermal conductivity than the implant housing.

Another measure relating to the thermal properties of a material is thermal mass. Thermal mass is a measure of an object's ability to absorb thermal energy. An object with a higher thermal mass is able to absorb more thermal energy than an object with a lower thermal mass. Thus, for a fixed amount of thermal energy applied to two different objects having different thermal masses, the object with the higher thermal mass will experience a smaller increase in temperature than the object with the lower thermal mass, i.e., the object with the lower thermal mass will be hotter than the object with the higher thermal mass. In the context of the cochlear implants described herein, there is provided an implant body having a much higher thermal mass than an electrode tip.

Because thermal energy preferentially follow paths with high thermal conductivity, embodiments where the electrode tip 208 has a lower thermal conductivity than the implant housing will cause thermal energy generated by RF-induced currents in the electrode lead 209 to flow toward the implant housing rather than toward the electrode tip 208. And because the implant body has a much higher thermal mass than the electrode tip 208, the implant housing is better able to absorb the thermal energy generated by the RF-induced currents than the electrode tip 208.

In some embodiments, the insulation or insulating sleeve 210 surrounding the conducting pathway 214 is made from certain materials and/or constructed in such a way (e.g., combinations of thickness and hardness) so as to have a sufficiently high thermal conductivity and/or have sufficient thermal conduction to cause at least some thermal energy generated by RF field-induced currents in the conducting pathway 214 to flow into the insulation or insulating sleeve 210 rather than to the electrode tip 208. The thermal conductivity of the insulation or insulating sleeve 210 is generally proportional to the hardness of the material from which the insulation or insulating sleeve 210 is constructed. As a general matter, thermal conductivity is a property of the material, and thermal conductivity does not change as the thickness of the material changes. Instead, the amount of thermal conduction will increase as the material is made thinner. Therefore, increasing the hardness of the insulating material, decreasing the thickness of the insulating material, or both, will increase thermal conduction of the insulation or insulating sleeve 210.

In some embodiments, the material comprising the insulation or insulating sleeve 210 includes one or more silicone elastic polymers (sometimes called silicone elastomers) having thermal conductivities of about 0.13 W/m·K to 0.4 W/m·K., such as carbon-filled Polyether ether ketone (PEEK) polymers, Polytetrafluoroethylene (PTFE) polymers, and/or Polysulfone (PES) polymers. In some embodiments, the insulation or insulating sleeve 210 is a silicone elastomer having a thickness of about 300 microns and a Shore A hardness of about 40. In further embodiments, the insulation or insulating sleeve 210 is a silicone elastomer having a thickness of about 100 microns and a Shore A hardness of about 80. In still further embodiments, the insulation or insulating sleeve 210 is PTFE or PES having a thickness of about 10 microns. In other embodiments, the thickness and hardness of the insulation or insulating sleeve 210 and the materials comprising the insulation or insulating sleeve 210 may vary, so long as the thermal conductivity and thermal conduction properties of the insulation or insulating sleeve 210 cause at least some thermal energy generated by RF field-induced currents in the conducting pathway 214 to flow into the insulation or insulating sleeve 210 rather than to the electrode tip 208. In some embodiments, a filler material is disposed between the conductive pathway and the insulation or insulating sleeve 210 to increase thermal conductance.

Figure 3:
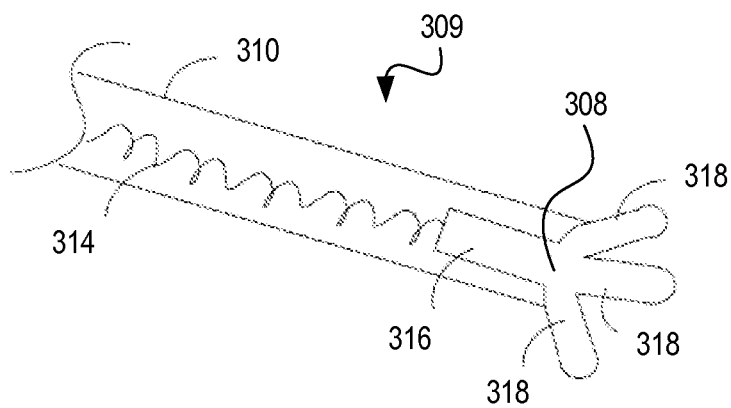
FIG. 3 shows another example of an electrode lead with an electrode tip configuration according to some embodiments.

FIG. 3 shows another example of an extra-cochlear electrode lead 309 with an electrode tip 308 having a set of protruding members 318 according to some embodiments.

One main difference between the configuration shown in FIG. 3 and the configuration shown in FIG. 2 is that the electrode tip 308 has a thermal mass enhancing structure. In particular, the electrode tip 308 has a set of protruding members 318, and the electrode tip 308 with the set of protruding members of FIG. 3 has a higher thermal mass than the electrode tip 208 shown in FIG. 3. As described above, thermal mass is a measure of an object's ability to absorb thermal energy, and an object with a higher thermal mass will experience a smaller increase in heat than an object with a lower thermal mass when both objects are exposed to the same amount of thermal energy. Because the electrode tip 308 with the protruding members 318 of FIG. 3 has a higher thermal mass than the electrode tip 208 of FIG. 2, the electrode tip 308 with the protruding members 318 of FIG. 3 will not get as hot as the electrode tip 208 of FIG. 2 if both configurations are exposed to the same amount of thermal energy. The embodiment in FIG. 3 shows three protruding members 318 in a branch-like configuration. However, more or fewer protruding members, or different configurations (e.g., star-shaped, hook-shaped, etc.) of protruding members could be used as well. The increased thermal mass configuration shown in FIG. 3 can be implemented alone or in combination with the features and functions of the other elements of the extra-cochlear electrode lead 309.

The various embodiments of the configuration shown in FIG. 3 are substantially similar in most all respects to the embodiments of the configuration shown and described with respect to the FIG. 2. For example, like the extra-cochlear electrode lead 209 shown in FIG. 2, the extra-cochlear electrode lead 309 of FIG. 3 also includes a conducting pathway 314 enclosed within insulation or an insulating sleeve 310. The proximal end (not shown) of the conducting pathway 314 is connected to stimulation circuitry in the implant housing. Like conducting pathway 214, conducting pathway 314 is an electrically conductive wire or similar structure made from a conductive material, such as platinum for example, and it provides an electrically conductive path between the stimulation circuitry within the implant housing and the electrode tip 308, which is coupled to the conducting pathway 314 via a crimp 316 or other similar connection mechanism.

Also like electrode tip 208, in some embodiments, the electrode tip 309 and its set of protruding members 318 are made from a metal or metal alloy having a thermal conductivity that is lower than the thermal conductivity of the implant housing. In one embodiment, for example, the electrode tip 308 and protruding members 318 are made at least partially from a titanium alloy (e.g., titanium grade 5, titanium grade 23, or other biocompatible titanium alloy) having a thermal conductivity of about 7.2 watts per meter kelvin (W/m·K) or less, and the implant housing is configured to have a thermal conductivity value of about 70 W/m·K. In another embodiment, for example, the electrode tip 308 and protruding members 318 are made from commercially-pure titanium, which has a thermal conductivity of about 16.3 W/m·K to about 21.6 W/m·K. In still other embodiments, the electrode tip 308 and protruding members 318 are made from steel, which has a thermal conductivity of about 16.0 W/m·K. Other combinations of materials selected for the electrode tip 308, the protruding members 318, and the housing materials are possible as well.

Additionally, in some embodiments, the insulation or insulating sleeve 310 surrounding the conducting pathway 314 is made from certain materials and/or constructed in such a way (e.g., combinations of thickness and hardness) so as to have thermal conductivity and/or thermal conduction properties that cause at least some thermal energy generated by RF field-induced currents in the conducting pathway 314 to flow into the insulation or insulating sleeve 310 rather than to the electrode tip 308 or its protruding members 318. For example, in various embodiments, the insulation or insulating sleeve 310 is constructed from materials that: (i) include one or more silicone elastic polymers (sometimes called silicone elastomers) having thermal conductivities of about 0.13 W/m·K to 0.4 W/m·K., such as carbon-filled Polyether ether ketone (PEEK) polymers, Polytetrafluoroethylene (PTFE) polymers, and/or Polysulfone (PES) polymers; (ii) have a thickness of about 10 to 300 microns; and/or (iii) have a Shore A hardness of about 40 to 80. In other embodiments, the thickness and hardness of the insulation or insulating sleeve 310 and the materials comprising the insulation or insulating sleeve may vary so long as the thermal conductivity and thermal conduction properties of the insulation or insulating sleeve 310 cause at least some thermal energy generated by RF field-induced currents in the conducting pathway 314 to flow into the insulation or insulating sleeve 310 rather than to the electrode tip 308 and its protruding members 318.

Figure 4A:
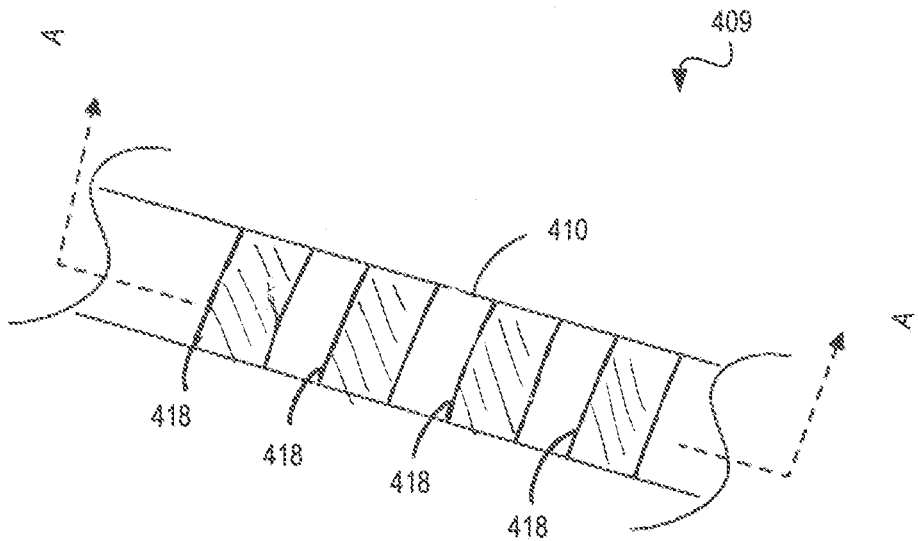
FIG. 4A shows an example of an electrode lead having an array of electrode pads or terminals according to some embodiments.
Figure 4B:
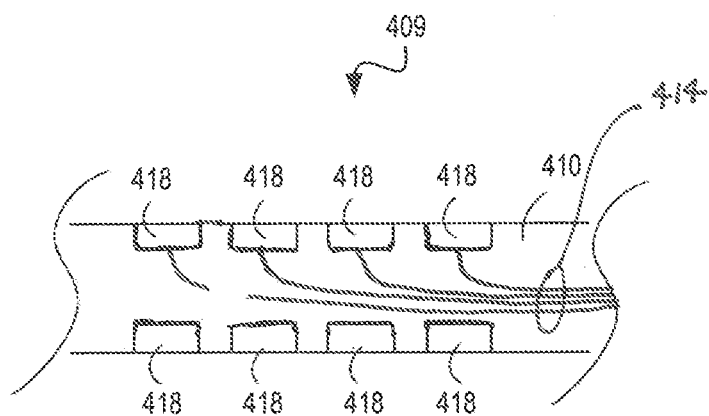
FIG. 4B shows a cross-sectional view of the configuration shown FIG. 4A.

FIG. 4A shows an example of an intracochlear electrode lead 409 having a plurality of intra-cochlear electrode pads or terminals 418, and FIG. 4B shows a cross-sectional view of the configuration shown in FIG. 4A.

FIG. 4A shows a perspective view of a portion of an intra-cochlear electrode lead 409 having a plurality of intra-cochlear electrode pads or terminals 418, each being electrically coupled to a conducting pathway 414 (FIG. 4B). In some embodiments, the electrode pads or terminals 418 are constructed from titanium or a titanium alloy similar to the electrode tips 208 (FIG. 2) and 308 (FIG. 3). However, in other embodiments, the electrode pads or terminals 418 are constructed from other types of biocompatible and electrically conductive materials. The plurality of intra-cochlear electrode pads or terminals 418 are arranged on, or integrated into an insulating carrier member 410.

FIG. 4B is a cross-sectional view of the intra-cochlear electrode lead 409, taken along cross-section A-A. As shown in FIG. 4B, individual electrode pads or terminals 418 are electrically coupled to their respective conducting pathway 414. The proximal ends (not shown) of the conducting pathways 414 are connected to stimulation circuitry enclosed within an implant housing. Similar to conducting pathway 214 (FIG. 2), each conducting pathway 414 is an electrically conductive wire or similar structure made from a conductive material, such as platinum for example.

Similar to electrode tip 208, in some embodiments, individual electrode pads or terminals 418 are made from a metal or metal alloy having a thermal conductivity that is lower than the thermal conductivity of the implant housing. In one embodiment, individual electrode pads or terminals 418 are made at least partially from a titanium alloy (e.g., titanium grade 5, titanium grade 23, or other biocompatible titanium alloy) having a thermal conductivity of about 7.2 watts per meter kelvin (W/m·K) or less, and the implant housing is configured to have a thermal conductivity value of about 70 W/m·K. In another embodiment, the electrode pads or terminals 418 are made from commercially-pure titanium, which has a thermal conductivity of about 16.3 W/m·K to about 21.6 W/m·K. In still another embodiment, the electrode pads or terminals 418 are made from steel, which has a thermal conductivity of about 16.0 W/m·K.

Additionally, in some embodiments, the insulating carrier member 410 surrounding the conducting pathways 414, is made from certain materials and/or constructed in such a way (e.g., combinations of thickness and hardness) so as to have thermal conductivity and/or thermal conduction properties that cause at least some thermal energy generated by RF field-induced currents in the conducting pathway 414 to flow into the insulating carrier member 410 rather than to the electrode pads or terminals 418. For example, in various embodiments, the insulating carrier member 410 is constructed from materials that: (i) include one or more silicone elastic polymers (sometimes called silicone elastomers) having thermal conductivities of about 0.13 W/m·K to 0.4 W/m·K., such as carbon-filled Polyether ether ketone (PEEK) polymers, Polytetrafluoroethylene (PTFE) polymers, and/or Polysulfone (PES) polymers; (ii) have a thickness of about 10 to 300 microns; and/or (iii) have a Shore A hardness of about 40 to 80. In other embodiments, the thickness and hardness of the insulating carrier member 410 and the materials comprising the insulating carrier member 410 may vary so long as the thermal conductivity and thermal conduction properties of the insulating carrier member 410 cause at least some thermal energy generated by RF field-induced currents in the conducting pathways 414 to flow into the insulating carrier member 410 rather than the electrode pads or terminals 418.

The various aspects and embodiments disclosed herein are for purposes of illustration and are not intended to be limiting, with the true scope being indicated by the following claims. Moreover, some features and functions have been described with respect to cochlear implants and, more generally, to hearing prostheses. However, the features and functions are equally applicable to other types of prostheses that include electrode leads that can be configured to stimulate organs or tissues of a prosthesis recipient via an array of one or more electrodes, such as cardiac pacemakers, brain stimulation prostheses, nerve stimulation prostheses, muscle stimulation prostheses, and the like. More generally, some of the features and functions described herein can be applied to any type of implantable prosthesis with an electrically conductive member that has two ends where one end is smaller than the other end.

What is claimed is:

1. A prosthesis comprising:
an implant housing enclosing stimulation circuitry; and
an electrode lead comprising a conducting pathway and an electrode tip at one end of the electrode lead, wherein the conducting pathway is configured to connect the stimulation circuitry with the electrode tip, wherein insulation encloses at least a portion of the electrode lead, wherein the electrode tip has a lower thermal conductivity relative to the implant housing, and wherein the thermal conductivity of the electrode tip is less than or equal to about 7.2 watts per meter Kelvin (W/m·K).

2. The prosthesis of claim 1, wherein the electrode tip comprises at least one of titanium or a titanium alloy.

3. The prosthesis of claim 1, wherein where the thermal conductivity and thermal conduction properties of the insulation cause at least some thermal energy in the conducting pathway to flow into the insulation rather than to the electrode tip.

4. The prosthesis of claim 1, wherein the insulation has at least one of (i) a thickness of less than or equal to about 100 microns and (ii) a Shore A hardness of greater than or equal to about 80.

5. The prosthesis of claim 1, wherein the insulation comprises at least one of: (i) a carbon-filled Polyether ether ketone (PEEK) polymer, (ii) a Polytetrafluoroethylene (PTFE) polymer, or (iii) a Polysulfone (PES) polymer.

6. The prosthesis of claim 1, wherein at least one of the electrode tip or the electrode lead includes at least one thermal mass enhancing structure.

7. A prosthesis comprising:
an implant housing enclosing circuitry; and
an electrode lead extending from the implant housing and comprising an insulating sleeve enclosing at least a portion of a conducting pathway connecting the circuitry with an electrode terminal positioned on the electrode lead distal to the implant housing, wherein the thermal conductivity and thermal conduction properties of the insulating sleeve cause at least some thermal energy in the conducting pathway to flow into the insulating sleeve rather than to the electrode terminal, and wherein the electrode terminal has a lower thermal conductivity relative to the implant housing.

8. The prosthesis of claim 7, wherein the insulating sleeve has a thermal conductivity of about 0.13 W/m·K to 0.4 W/m·K.

9. The prosthesis of claim 7, wherein the insulating sleeve has one of: (i) a thickness of less than about 300 microns and a Shore A hardness of about 40; (ii) a thickness of about 100 microns and a Shore A hardness of about 80; or (iii) a thickness of about 10 microns.

10. The prosthesis of claim 7, wherein the insulating sleeve comprises at least one of (i) a carbon-filled Polyether ether ketone (PEEK) polymer, (ii) a Polytetrafluoroethylene (PTFE) polymers, and/or (iii) a Polysulfone (PES) polymer.

11. The prosthesis of claim 7, further comprising a filler material disposed between the conductive pathway and the insulating sleeve.

12. The prosthesis of claim 7, wherein the electrode terminal has a thermal conductivity less than or equal to about 7.2 W/m·K, and wherein the implant housing has a thermal conductivity of about 70 W/m·K.

13. The prosthesis of claim 7, wherein the electrode terminal includes a plurality of protruding members.

14. The prosthesis of claim 7, wherein the electrode lead is one of a plurality of electrode leads terminating in a plurality of corresponding electrode pads disposed along the surface of the insulating sleeve.

15. A medical device comprising:
a component configured for implantation in a recipient; and
an electrically conductive elongate member extending from the component and terminating at a tip that is smaller than the component, wherein the tip comprises a material having a lower thermal conductivity relative to the component, and wherein at least one of the tip or the elongate member includes at least one thermal mass enhancing structure.

16. The medical device of claim 15, further comprising:
insulation enclosing at least a portion of the elongate member, wherein the insulation has thermal conductivity and thermal conduction properties that cause at least some thermal energy in the elongate member to flow into the insulation rather than the tip.

17. The medical device of claim 16, wherein the insulation comprises at least one of (i) a silicone elastomer having a thickness of about 300 microns and a Shore A hardness of about 40, (ii) a silicone elastomer having a thickness of about 100 microns and a Shore A hardness of about 80, or (iii) a Polytetrafluoroethylene (PTFE) polymer or a Polysulfone (PES) polymer having a thickness of about 10 microns.

18. The medical device of claim 15, wherein the thermal conductivity of the tip material is about 7.2 W/m·K.

* * * * *